United States Patent
Schoepgens et al.

(10) Patent No.: US 10,646,418 B2
(45) Date of Patent: *May 12, 2020

(54) AFTERTREATMENT AGENT FOR THE REDUCTIVE DECOLORIZATION OF DYED KERATINIC FIBERS

(71) Applicant: Henkel AG & Co. KGaA, Duesseldorf (DE)

(72) Inventors: Juergen Schoepgens, Schwalmtal (DE); Burkhard Mueller, Duesseldorf (DE); Constanze Neuba, Grevenbroich (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/609,149

(22) Filed: May 31, 2017

(65) Prior Publication Data

US 2017/0348205 A1 Dec. 7, 2017

(30) Foreign Application Priority Data

Jun. 7, 2016 (DE) ........................ 10 2016 209 980

(51) Int. Cl.

| | | |
|---|---|---|
| *A61K 8/20* | (2006.01) | |
| *A61K 8/21* | (2006.01) | |
| *A61K 8/23* | (2006.01) | |
| *A61K 8/46* | (2006.01) | |
| *A61Q 5/08* | (2006.01) | |
| *A61K 8/24* | (2006.01) | |
| *A61K 8/36* | (2006.01) | |
| *A61K 8/365* | (2006.01) | |
| *A61K 8/19* | (2006.01) | |
| *A61K 8/60* | (2006.01) | |
| *A61K 8/362* | (2006.01) | |

(52) U.S. Cl.
CPC .................. *A61K 8/20* (2013.01); *A61K 8/19* (2013.01); *A61K 8/21* (2013.01); *A61K 8/23* (2013.01); *A61K 8/24* (2013.01); *A61K 8/36* (2013.01); *A61K 8/362* (2013.01); *A61K 8/365* (2013.01); *A61K 8/46* (2013.01); *A61K 8/60* (2013.01); *A61Q 5/08* (2013.01)

(58) Field of Classification Search
None
See application file for complete search history.

(56) References Cited

FOREIGN PATENT DOCUMENTS

| EP | 1300136 A2 | 4/2003 |
|---|---|---|
| WO | 2008055756 A1 | 5/2008 |
| WO | 2012069599 A2 | 5/2012 |
| WO | 2013017862 A2 | 2/2013 |
| WO | 2014174230 A2 | 10/2014 |

OTHER PUBLICATIONS

Schrader, K., "Basics and recipes of cosmetics", Second Improved and Extended Edition, 1989, Huethig Buch Verlag, Heidelberg, Germany.

*Primary Examiner* — Nicole P Babson
(74) *Attorney, Agent, or Firm* — Lorenz & Kopf, LLP

(57) ABSTRACT

Cosmetic agents for treating keratinic fibers and methods for the reductive decolorization of dyed keratinic fibers are provided herein. In an embodiment, a cosmetic agent for treating keratinic fibers includes (a) one or more metal salts chosen from the group of tin(II) salts, iron(II) salts, manganese(II) salts, titanium(II) salts, or titanium(III) salts and (b) water. The agent has a pH between about 1.0 and about 3.0.

8 Claims, No Drawings

AFTERTREATMENT AGENT FOR THE REDUCTIVE DECOLORIZATION OF DYED KERATINIC FIBERS

CROSS-REFERENCE TO RELATED APPLICATION

This application claims priority to German Patent Application No. 10 2016 209 980.9, filed Jun. 7, 2016, which is incorporated herein by reference in its entirety.

TECHNICAL FIELD

The present disclosure is directed to the field of cosmetics, and relates to a water-containing cosmetic agent for treating keratinic fibers, in particular human hair, containing one or more metal salts from the group of tin(II) salts, iron(II) salts, manganese(II) salts, titanium(II) salts, and titanium(III) salts, and having a pH between about 1.0 and about 3.0. This agent is used as contemplated herein as an aftertreatment agent after the reductive decolorization of artificially colored keratinic fibers.

A further subject matter of the present disclosure is a method for the reductive decolorization of dyed keratin fibers, in particular human hair, in which the above-described aftertreatment agent is used.

Preparations for tinting and dyeing hair are an important type of cosmetic agent. They may be used for shading the natural hair color lighter or darker according to the desires of the person in question to achieve a totally different hair color, or to cover undesirable color shades such as gray. Depending on the desired color or durability of the coloration, common hair dyes are formulated on the basis of either oxidation dyes or substantive dyes. Combinations of oxidation dyes and substantive dyes are also often used to achieve special shades.

Coloring agents based on oxidation dyes result in brilliant, long-lasting color shades. However, they require the use of strong oxidizing agents such as hydrogen peroxide. Such coloring agents contain oxidation dye precursors, so-called developer components and coupler components. The developer components form the actual dyes with one another under the influence of oxidizing agents or atmospheric oxygen, or by coupling with one or more coupler components.

Coloring agents based on substantive dyes are frequently used for temporary colorings. Substantive dyes are dye molecules that are directly absorbed onto the hair, and require no oxidative process to form the color. Examples of important representatives of this dye class are triphenylmethane dyes, azo dyes, anthraquinone dyes, or nitrobenzene dyes, which in each case may also bear cationic or anionic groups.

In all of these coloring processes, it may be desired to completely or partially undo the coloration for various reasons. Partial removal of the coloration may be appropriate, for example, when the color result on the fibers turns out darker than desired. On the other hand, complete removal of the coloration may be desired in some cases. It is thus conceivable, for example, for the hair to be dyed or tinted in a certain shade for a specific occasion, and returned to the original color after a few days.

Various agents and methods for color removal are already known from the literature. One method for undoing colorations that is well known from the prior art is the oxidative decolorization of the dyed hair, for example using a customary bleaching agent. However, in this process the fibers may be damaged by the use of strong oxidizing agents.

Furthermore, reductive processes for color removal have already been described. Thus, for example, European Patent application EP 1 300 136 A2 discloses methods for hair treatment in which the hair is dyed in a first step and is reductively decolorized in a second step. The reductive decolorization takes place by applying a formulation containing a dithionite salt and a surfactant. In WO 2008/055756 A2, the reductive decolorization of keratin fibers is carried out using a mixture of a reducing agent and an absorption agent.

The publications WO 2012/069599, WO 2014/174230, and WO 2013/017862 describe various sulfinic acid derivatives in agents for the removal of color from dyed hair.

When reductive decolorizing agents are used, the decolorization takes place by reduction of the dyes that are present on the keratin fibers or hairs. As a result of the reduction, the dyes are generally converted to their reduced leuco forms. In this process, the double bonds present in the dyes are reduced, the chromophoric system of the dyes is thus disrupted, and the dye is converted to a colorless form.

A general problem with the reductive decolorizing agents known from the prior art is that, due to use of the reducing agent, although the dyed keratin fibers may initially be decolorized, the color removal is short-lived. In particular for oxidatively dyed hair in which the coloration is produced on the hair by oxidation dye precursors of the developer type and the coupler type, colorations are obtained which sometimes have very good fastness properties. When the reductive decolorizing agent is applied, these dyes are then reductively converted to colorless compounds, which, however, still remain on the hair due to similarly good fastness properties.

After the reducing agent is rinsed off, and under the action of atmospheric oxygen, these reduced forms may then be gradually reoxidized. As a result of this reoxidation, fairly pronounced back-staining takes place. This back-staining generally does not correspond to the shade in which the keratin fibers were previously dyed, and instead may turn out to be unattractive in some cases, and therefore is even less desired by the user of the decolorizing agent.

BRIEF SUMMARY

Cosmetic agents for treating keratinic fibers and methods for the reductive decolorization of dyed keratinic fibers are provided herein. In an embodiment, a cosmetic agent for treating keratinic fibers includes (a) one or more metal salts chosen from the group of tin(II) salts, iron(II) salts, manganese(II) salts, titanium(II) salts, or titanium(III) salts and (b) water. The agent has a pH between about 1.0 and about 3.0.

In another embodiment, a method for the reductive decolorization of dyed keratinic fibers includes the following steps in the stated sequence:

(I) applying a decolorizing agent, comprising at least one sulfur-containing reducing agent, to keratinic fibers, (II) allowing the decolorizing agent to act, (III) optionally rinsing the decolorizing agent from the keratinic fibers, (IV) applying an aftertreatment agent to the keratinic fibers, wherein the aftertreatment agent is an agent comprising (a) one or more metal salts chosen from the group of tin(II) salts, iron(II) salts, manganese(II) salts, titanium(II) salts, or titanium(III) salts and (b) water, wherein the aftertreatment agent has a pH between 1.0 and 3.0, (V) allowing the aftertreatment agent to act for a period of 30 seconds to 45 minutes, and (VI) optionally rinsing the aftertreatment agent from the keratinic fibers.

In another embodiment, a cosmetic agent for treating keratinic fibers includes (a) one or more metal salts chosen from the group of tin(II) salts, iron(II) salts, manganese(II) salts, titanium(II) salts, or titanium(III) salts. The (a) one or more metal salts are present in an overall quantity of from about 3.0 to about 10.0% by weight, based on the total weight of the agent. The agent further includes (b) water. The (b) water is present in an overall quantity of from about 70 to 93.0% by weight, based on the total weight of the agent. The agent further includes (c) one or more acids chosen from the group of inorganic acids or organic acids. The agent further includes (d) one or more surfactants chosen from the group of nonionic, anionic, zwitterionic, amphoteric, or cationic surfactants. The overall quantity of aromatic compounds present in the agent is less than about 0.01% by weight, based on the total weight of the agent. An overall quantity of oxidizing agents chosen from the group of peroxo compounds is present in the agent in an amount less than about 0.01% by weight, based on the total weight of the agent. The agent has a pH between about 1.0 and about 2.5.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure is to provide an agent that allows the decolorizing power of reductive color removal agents to be further improved. The aim of using the agent is that the decolorizing effect of a customary sulfur-containing reducing agent known from the prior art is further improved and lasts longer, and that no back-staining, alteration in shade, or darkening occurs under the action of atmospheric oxygen.

It has surprisingly now been found that this object may be achieved by using an aftertreatment agent that is applied to the keratinic fibers after application of a reductive decolorizing agent. This aftertreatment agent has a content of one or more metal salts from the group of tin(II) salts, iron(II) salts, manganese(II) salts, titanium(II) salts, and titanium(III) salts that are present in an aqueous cosmetic carrier formulation that is set to a strongly acidic pH. Due to this aftertreatment of the reductively decolorized fibers with the metal salts in aqueous solution, it has been unforeseeably possible to further improve the decolorizing result, and also to effectively inhibit the reoxidation of the dyes (i.e., the darkening that takes place under the action of atmospheric oxygen).

A first subject matter of the present disclosure is a cosmetic agent for treating keratinic fibers, in particular human hair, containing (a) one or more metal salts from the group of tin(II) salts, iron(II) salts, manganese(II) salts, titanium(II) salts, and titanium(III) salts and (b) water, wherein the agent has a pH between about 1.0 and about 3.0.

The agent of the first subject matter as contemplated herein is applied as contemplated herein as an aftertreatment agent after application of a reductive decolorizing agent to the keratinic fibers.

In other words, the agent is thus a cosmetic agent for the aftertreatment of reductively decolorized keratinic fibers, in particular human hair, containing (a) one or more metal salts from the group of tin(II) salts, iron(II) salts, manganese(II) salts, titanium(II) salts, and titanium(III) salts and (b) water, wherein the agent has a pH between about 1.0 and about 3.0.

The term "dyed keratinic fibers" is understood to mean keratin fibers that have been dyed with conventional cosmetic coloring agents known to those skilled in the art. In particular, "dyed keratinic fibers" is understood to mean fibers that have been dyed with the oxidative coloring agents known from the prior art and/or with substantive dyes. In this regard, explicit reference is made to the known monographs, for example Kh. Schrader, Grundlagen and Rezepturen der Kosmetika [Fundamentals and Formulations in Cosmetics], 2nd Edition, Huthig Buch Verlag, Heidelberg, 1989, which reflect the relevant knowledge of those skilled in the art.

Accordingly, "reductively decolorized keratinic fibers" are understood to mean dyed keratinic fibers that have been decolorized by applying a sulfur-containing reducing agent.

Agents for the aftertreatment of reductively decolorized keratinic fibers

Keratinic fibers dyed with synthetic dyes (oxidative and/or substantive dyes, for example) may be reductively decolorized by applying a sulfur-containing reducing agent. Accordingly, a reductive decolorizing agent is understood to mean an agent that contains one or more sulfur-containing reducing agents.

As sulfur-containing reducing agents, it is possible to use, for example, one or more compounds selected from the group comprising formamidine sulfinic acid ((H2N)(NH)C(SO2H)), sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethanesulfinic acid, aminomethanesulfinic acid, cysteine, thiolactic acid, thioglycolic acid, disodium [(sulfinatomethyl)amino]methanesulfinate (HN(CH2SO2Na)2), dipotassium [(sulfinatomethyl)amino]methanesulfinate (HN(CH2SO2K)2), [(sulfinomethyl)amino]methanesulfinic acid (HN(CH$_2$SO$_2$H)$_2$), trisodium [bis(sulfinatomethyl)amino]methanesulfinate (N(CH$_2$SO$_2$Na)$_3$), tripotassium [bis(sulfinatomethyl)amino]methanesulfinate (N(CH$_2$SO$_2$K)$_3$), [bis(sulfinomethyl)amino]methanesulfinic acid (N(CH$_2$SO$_2$H)$_3$), sodium 1-aminoethane-1-sulfinate (H$_2$NCH(CH$_3$)SO$_2$Na), potassium 1-aminoethane-1-sulfinate (H$_2$NCH(CH$_3$)SO$_2$K), 1-aminoethane-1-sulfinic acid (H$_2$NCH(CH$_3$)SO$_2$H), disodium 1-[(1-sulfinatoethyl)amino]ethane-1-sulfinate (HN(CH(CH$_3$)SO$_2$Na)$_2$), dipotassium 1-[(1-sulfinatoethyl)amino]ethane-1-sulfinate (HN(CH(CH$_3$)SO$_2$K)$_2$), 1-[(1-sulfinoethyl)amino]ethane-1-sulfinic acid (HN(CH(CH$_3$)SO$_2$H)$_2$), trisodium 1-[bis(1-sulfinatoethyl)amino]ethane-1-sulfinate (N(CH(CH$_3$)SO$_2$Na)$_3$), tripotassium 1-[bis(1-sulfinatoethyl)amino]ethane-1-sulfinate (N(CH(CH$_3$)SO$_2$K)$_3$), and 1-[bis(1-sulfinoethyl)amino]ethane-1-sulfinic acid (N(CH(CH$_3$)SO$_2$H)$_3$).

Formamidine sulfinic acid is alternatively referred to as thiourea dioxide or aminoiminomethanesulfinic acid. Formamidine sulfinic acid has the structure of formula (I), but may also be present in the form of its tautomers. Formamidine sulfinic acid has CAS No. 1758-73-2, and is commercially available from various suppliers, for example Sigma Aldrich.

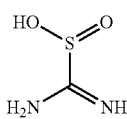

(I)

Sodium dithionite is an inorganic reducing agent with the empirical formula Na$_2$S$_2$O$_4$ and CAS No. 7775-14-6.

Zinc dithionite is an inorganic reducing agent with the empirical formula ZnS$_2$O$_4$ and CAS No. 7779-86-4.

Potassium dithionite is an inorganic reducing agent with the empirical formula K$_2$S$_2$O$_4$ and CAS No. 14293-73-3.

Sodium sulfite is an inorganic reducing agent with the empirical formula Na$_2$SO$_3$ and CAS No. 7757-83-7.

Sodium hydrogen sulfite is an inorganic reducing agent with the empirical formula NaHSO$_3$ and CAS No. 7631-90-5. Sodium hydrogen sulfite is preferably used in the form of an aqueous solution.

Potassium sulfite is an inorganic reducing agent with the empirical formula K$_2$SO$_3$ and CAS No. 10117-38-1.

Potassium hydrogen sulfite is an inorganic reducing agent with the empirical formula KHSO$_3$ and CAS No. 7773-03-7.

Ammonium sulfite is an inorganic reducing agent with the empirical formula (NH$_4$)$_2$SO$_3$ and CAS No. 10196-04-0.

Sodium thiosulfate is an inorganic reducing agent with the empirical formula Na$_2$S$_2$O$_3$ and CAS No. 7772-98-7.

Potassium thiosulfate is an inorganic reducing agent with the empirical formula K$_2$S$_2$O$_3$ and CAS No. 10294-66-3.

Ammonium thiosulfate is an inorganic reducing agent with the empirical formula (NH$_4$)$_2$S$_2$O$_3$ and CAS No. 7783-18-8.

Hydroxymethanesulfinic acid is an organic reducing agent with the formula HO—CH$_2$—HO—CHh and CAS No. 79-25-4. Hydroxymethanesulfinic acid is alternatively referred to as formaldehyde sulfoxylic acid. Use of hydroxymethanesulfinic acid itself as well as use of the physiologically acceptable salts of hydroxymethanesulfinic acid, for example the sodium salt and/or the zinc salt, are encompassed by the present disclosure. Accordingly, the use of sodium formaldehyde sulfoxylate (sodium hydroxymethanesulfinate, the sodium salt of hydroxymethanesulfinic acid) and/or zinc formaldehyde sulfoxylate (zinc hydroxymethanesulfinate, the zinc salt of hydroxymethanesulfinic acid) is likewise encompassed by the present disclosure.

Aminomethanesulfinic acid is an organic reducing agent with the formula H$_2$N—CH$_2$—CH th and CAS No. 118201-33-5. Use of aminomethanesulfinic acid itself as well as use of the physiologically acceptable salts of aminomethanesulfinic acid, for example the sodium salt and/or the zinc salt, are encompassed by the present disclosure. The use of sodium aminomethanesulfinate (the sodium salt of aminomethanesulfinic acid) and/or zinc aminomethanesulfinate (the zinc salt of aminomethanesulfinic acid) is therefore likewise encompassed by the present disclosure.

As contemplated herein, cysteine (2-amino-3-sulfanyl-propionic acid) is understood to mean d-cysteine, l-cysteine, and/or a mixture of d- and l-cysteine.

Thiolactic acid (2-sulfanylpropionic acid) is understood to mean D-thiolactic acid, L-thiolactic acid, and/or a mixture of D- and L-thiolactic acid. Use of thiolactic acid itself as well as use of thiolactic acid in the form of a physiologically acceptable salt thereof are encompassed by the present disclosure. Ammonium thiolactate is a preferred salt of thiolactic acid.

Ammonium thiolactate is the ammonium salt of thiolactic acid (i.e., the ammonium salt of 2-sulfanylpropionic acid) (formula II).

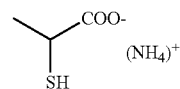

(Formula II)

By definition, ammonium thiolactate includes the ammonium salts of D-thiolactic acid as well as the ammonium salts of L-thiolactic acid, and the mixtures thereof.

Thioglycolic acid (sulfanylacetic acid, 2-mercaptoacetic acid) is understood to mean an organic reducing agent of the formula HS—CH$_2$—COOH; the compound has CAS No. 68-11-1. Also for thioglycolic acid, use of thioglycolic acid itself as well as use of a physiologically acceptable salt of thioglycolic acid are encompassed by the present disclosure. Sodium thioglycolate, potassium thioglycolate, and/or ammonium thioglycolate, for example, may be used as physiologically acceptable salts of thioglycolic acid. Ammonium thioglycolate is a preferred physiologically acceptable salt of thioglycolic acid.

Ammonium thioglycolate is the ammonium salt of thioglycolic acid (i.e., the ammonium salt of sulfanylacetic acid) (formula III).

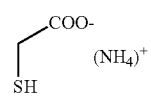

(Formula III)

Disodium[(sulfinatomethyDamino]methanesulfinate is the disodium salt of [(sulfinomethyl)amino]methanesulfinic acid and has the structure of formula (IV).

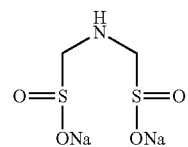

(IV)

Dipotassium[(sulfinatomethyl)amino]methanesulfinate is the dipotassium salt of [(sulfinomethyl)amino]methanesulfinic acid and has the structure of formula (V).

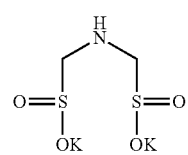

(V)

[(Sulfinomethyl)amino]methanesulfinic acid has the structure of formula (VI).

(VI)

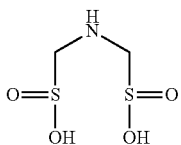

Trisodium[bis(sulfinatomethyl)amino]methanesulfinate is the trisodium salt of [bis(sulfinomethyl)amino]methanesulfinic acid and has the structure of formula (VII).

(VII)

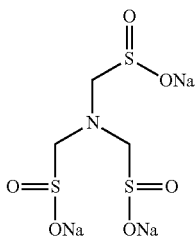

Tripotassium[bis(sulfinatomethyl)amino]methanesulfinate is the tripotassium salt of [bis(sulfinomethyl)amino]methanesulfinic acid and has the structure of formula (VIII).

(VIII)

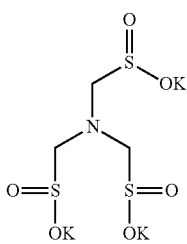

[Bis(sulfinomethyl)amino]methanesulfinic acid has the structure of formula (IX).

(IX)

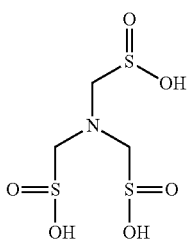

Sodium 1-aminoethane-1-sulfinate is the sodium salt of 1-aminoethane-1-sulfinic acid and has the structure of formula (X).

(X)

Potassium 1-aminoethane-1-sulfinate is the potassium salt of 1-aminoethane-1-sulfinic acid and has the structure of formula (XI).

(XI)

1. 1-Aminoethane-1-sulfinic acid has the structure of formula (XII).

(XII)

Disodium 1-[(1-sulfinatoethyl)amino]ethane-1-sulfinate is the disodium salt of 1-[(1-sulfinoethyl)amino]ethane-1-sulfinic acid and has the structure of formula (XIII).

(XIII)

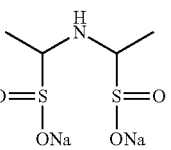

Dipotassium 1-[(1-sulfinatoethyl)amino]ethane-1-sulfinate is the dipotassium salt of 1-[(1-sulfinoethyl)amino]ethane-1-sulfinic acid and has the structure of formula (XIV).

(XIV)

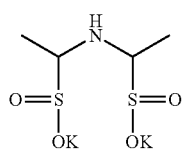

1-[(1-Sulfinoethyl)amino]ethane-1-sulfinic acid has the structure of formula (XV).

(XV)

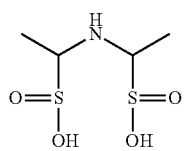

Trisodium 1-[bis(1-sulfinatoethyl)amino]ethane-1-sulfinate is the trisodium salt of 1-[bis(1-sulfinoethyl)amino]ethane-1-sulfinic acid and has the structure of formula (XVI).

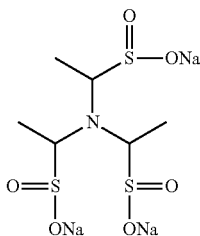

(XVI)

Tripotassium 1-[bis(1-sulfinatoethyl)amino]ethane-1-sulfinate is the tripotassium salt of 1-[bis(1-sulfinoethyl)amino]ethane-1-sulfinic acid and has the structure of formula (XVII).

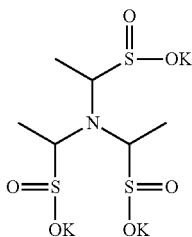

(XVII)

1-[Bis(1-sulfinoethyl)amino]ethane-1-sulfinic acid has the structure of formula (XVIII).

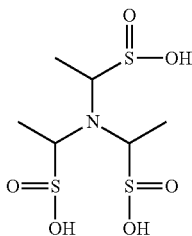

(XVIII)

Preparation of the compounds of formulas (IV) through (XVIII) is described in EP 0914516 B1, for example.

The above-mentioned sulfur-containing reducing agents bring about the reduction of the dyes present on the keratin fibers or hairs. As a result of the reduction, the dyes are generally converted to their reduced leuco forms. In this process, the double bonds present in the dyes are reduced, the chromophoric system of the dyes is thus disrupted, and the dye is converted to a colorless form.

After the reducing agent is rinsed off, and under the action of atmospheric oxygen, these reduced forms may then be gradually reoxidized. Fairly pronounced back-staining takes place as a result of this reoxidation.

In the course of the studies leading to the present disclosure, it has been found that this reoxidation or back-staining of the decolorized keratin fibers may be effectively minimized or prevented when after applying, and optionally after rinsing off, the sulfur-containing reducing agents, an acidic aqueous formulation containing at least one metal salt from group (a) is applied to the keratin fibers. The metal salts (a) are selected from the group of tin(II) salts, iron(II) salts, manganese(II) salts, titanium(II) salts, and titanium(III) salts.

As the first component (a), the aftertreatment agents as contemplated herein contain one or more metal salts from the group of tin(II) salts, iron(II) salts, manganese(II) salts, titanium(II) salts, and titanium(III) salts.

The metal salts of this group (a) may be converted to a higher oxidation state, and thus have a reducing action on other compounds. Thus, for example, the tin(II) salts may be converted to tin(IV) salts. Iron(II) salts may be converted to iron(III) salts. Manganese(II) salts may be converted to manganese(IV) salts. Titanium(II) and titanium(III) salts may be converted to titanium(IV) salts. The conversion to a higher oxidation state takes place within the scope of a redox reaction in which the other participating reactant is reduced. It has been found that use of the agent, when it is applied as an aftertreatment agent following a reductive color removal treatment, effectively prevents darkening of the keratinic fibers. In this regard, it is presumed that the metal salts, due to their reducing potential, are able to prevent particularly well the reoxidation of the reduced dyes caused by atmospheric oxygen.

As contemplated herein, a metal salt is understood to mean a salt of the above-mentioned elements; i.e., the metal is present as a cation and is neutralized by the corresponding equivalent of anions specified by the oxidation state of the metal. The anion(s) may be inorganic or organic. Examples of inorganic anions are chloride, bromite, sulfate, hydrogen sulfate, carbonate, hydrogen carbonate, hydroxide, phosphate, and hydrogen phosphate. Examples of organic anions are formate, acetate, propionate, lactate, citrate, and tartrate.

Within the group of metal salts as contemplated herein, certain metal salts that improve the overall performance of the color removal and also inhibit the darkening of the decolorized keratin fibers particularly well and for a particularly long time have proven to be particularly effective. Tin(II) salts and iron(II) salts have proven to be particularly effective. The tin(II) salts are very particularly suited.

In one particularly preferred embodiment, an agent as contemplated herein contains (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate.

Tin(II) chloride has the empirical formula $SnCl_2$.
Tin(II) bromide has the empirical formula $SnBr_2$.
Tin(II) fluoride has the empirical formula $SnF_2$.
Tin(II) sulfate has the empirical formula $SnSO_4$.
Tin(II) oxide has the empirical formula $SnO$.
Tin(II) hydroxide has the empirical formula $Sn(OH)_2$.
Tin(II) carbonate has the empirical formula $Sn(CO_3)$.
Tin(II) phosphate is alternatively referred to as tin(II) pyrophosphate and has the empirical formula $Sn_2(P_2O_7)$.
Tin(II) acetate has the empirical formula $Sn(CH_3COO_2)_2$.
Tin(II) gluconate is the tin salt of gluconic acid and has the empirical formula $Sn(C_6H_{11}O_7)_2$.
Tin(II) lactate is the tin salt of lactic acid has the empirical formula $Sn(C_3H_5O_3)_2$.
Tin(II) tartrate is the tin salt of tartaric acid and has the empirical formula $Sn(C_4H_4O_6)$.
Tin(II) oxalate is the tin salt of oxalic acid has the empirical formula $Sn(C_2O_4)$.
Iron(II) chloride has the empirical formula $FeCl_2$.
Iron(II) bromide has the empirical formula $FeBr_2$.
Iron(II) fluoride has the empirical formula $FeF_2$.

Iron(II) sulfate has the empirical formula Fe(SO$_4$).
Iron(II) oxide has the empirical formula FeO.
Iron(II) hydroxide has the empirical formula Fe(OH)$_2$.
Iron(II) carbonate has the empirical formula Fe(CO$_3$).
Iron(II) phosphate has the empirical formula Fe$_3$(PO$_4$)$_2$.
Iron(II) acetate has the empirical formula Fe(CH$_3$COO$_2$)$_2$.
Iron(II) gluconate is the iron salt of gluconic acid and has the empirical formula Fe(C$_6$H$_{11}$O$_7$)$_2$.
Iron(II) lactate is the iron salt of lactic acid and has the empirical formula Fe(C$_3$H$_5$O$_3$)$_2$.
Iron(II) tartrate is the iron salt of tartaric acid and has the empirical formula Fe(C$_4$H$_4$O$_6$).
Iron(II) oxalate is the iron salt of oxalic acid and has the empirical formula Fe(C$_2$O$_4$).

The hydrates of the metal salts mentioned above are also encompassed by the present disclosure.

It has been possible to achieve the best effects with an agent that contains one or more tin(II) salts. The best color removal performance has been achieved when, following the use of a reductive decolorizing agent, an agent was applied to the keratinic fibers that contained one or more salts from the group comprising tin(II) chloride, tin(II) bromide, tin(II) fluoride, tin(II) acetate, tin(II) gluconate, tin(II) lactate, tin(II) tartrate, and tin(II) oxalate. In comparison to the dyed hair, the hair that was decolorized with a sulfur-containing reducing agent and then aftertreated with tin(II) salts (a) was the most strongly decolorized. When the strands decolorized in this way were stored in air, minor back-staining or reoxidation also occurred.

In one very particularly preferred embodiment, an agent as contemplated herein contains (a) one or more metal salts from the group comprising tin(II) chloride, tin(II) bromide, tin(II) fluoride, tin(II) acetate, tin(II) gluconate, tin(II) lactate, tin(II) tartrate, and tin(II) oxalate.

The metal salt(s) is/are preferably used in the agent as contemplated herein in certain quantity ranges. The agent preferably contains one or more metal salts (a) in an overall quantity of from about 0.5 to about 15.0% by weight, from about 1.0 to about 13.0% by weight, from about 2.0 to about 11.0% by weight, or from about 3.0 to about 10.0% by weight. The stated quantities refer to the total weight of all metal salts as contemplated herein from group (a) contained in the agent, set in relation to the total weight.

In one very particularly preferred embodiment, an agent as contemplated herein contains, based on the total weight of the agent,
one or more metal salts in an overall quantity of from about 0.5 to about 15.0% by weight, from about 1.0 to about 13.0% by weight, from about 2.0 to about 11.0% by weight, or from about 3.0 to about 10.0% by weight.

One very particularly preferred agent contains (a) from about 0.5 to about 15.0% by weight tin(II) chloride, based on the total weight of the agent.
One very particularly preferred agent contains (a) from about 1.0 to about 13.0% by weight tin(II) chloride, based on the total weight of the agent.
One very particularly preferred agent contains (a) from about 2.0 to about 11.0% by weight tin(II) chloride, based on the total weight of the agent.
One very particularly preferred agent contains (a) from about 3.0 to about 10.0% by weight tin(II) chloride, based on the total weight of the agent.
One very particularly preferred agent contains (a) from about 0.5 to about 15.0% by weight tin(II) bromide, based on the total weight of the agent.
One very particularly preferred agent contains (a) from about 1.0 to about 13.0% by weight tin(II) bromide, based on the total weight of the agent.
One very particularly preferred agent contains (a) from about 2.0 to about 11.0% by weight tin(II) bromide, based on the total weight of the agent.
One very particularly preferred agent contains (a) from about 3.0 to about 10.0% by weight tin(II) bromide, based on the total weight of the agent.
One very particularly preferred agent contains (a) from about 0.5 to about 15.0% by weight tin(II) fluoride, based on the total weight of the agent.
One very particularly preferred agent contains (a) from about 1.0 to about 13.0% by weight tin(II) fluoride, based on the total weight of the agent.
One very particularly preferred agent contains (a) from about 2.0 to about 11.0% by weight tin(II) fluoride, based on the total weight of the agent.
One very particularly preferred agent contains (a) from about 3.0 to about 10.0% by weight tin(II) fluoride, based on the total weight of the agent.
One very particularly preferred agent contains (a) from about 0.5 to about 15.0% by weight tin(II) acetate, based on the total weight of the agent.
One very particularly preferred agent contains (a) from about 1.0 to about 13.0% by weight tin(II) acetate, based on the total weight of the agent.
One very particularly preferred agent contains (a) from about 2.0 to about 11.0% by weight tin(II) acetate, based on the total weight of the agent.
One very particularly preferred agent contains (a) from about 3.0 to about 10.0% by weight tin(II) acetate, based on the total weight of the agent.
One very particularly preferred agent contains (a) from about 0.5 to about 15.0% by weight tin(II) gluconate, based on the total weight of the agent.
One very particularly preferred agent contains (a) from about 1.0 to about 13.0% by weight tin(II) gluconate, based on the total weight of the agent.
One very particularly preferred agent contains (a) from about 2.0 to about 11.0% by weight tin(II) gluconate, based on the total weight of the agent.
One very particularly preferred agent contains (a) from about 3.0 to about 10.0% by weight tin(II) gluconate, based on the total weight of the agent.
One very particularly preferred agent contains (a) from about 0.5 to about 15.0% by weight tin(II) lactate, based on the total weight of the agent.
One very particularly preferred agent contains (a) from about 1.0 to about 13.0% by weight tin(II) lactate, based on the total weight of the agent.
One very particularly preferred agent contains (a) from about 2.0 to about 11.0% by weight tin(II) lactate, based on the total weight of the agent.
One very particularly preferred agent contains (a) from about 3.0 to about 10.0% by weight tin(II) lactate, based on the total weight of the agent.
One very particularly preferred agent contains (a) from about 0.5 to about 15.0% by weight tin(II) tartrate, based on the total weight of the agent.
One very particularly preferred agent contains (a) from about 1.0 to about 13.0% by weight tin(II) tartrate, based on the total weight of the agent.
One very particularly preferred agent contains (a) from about 2.0 to about 11.0% by weight tin(II) tartrate, based on the total weight of the agent.

One very particularly preferred agent contains (a) from about 3.0 to about 10.0% by weight tin(II) tartrate, based on the total weight of the agent.

One very particularly preferred agent contains (a) from about 0.5 to about 15.0% by weight tin(II) oxalate, based on the total weight of the agent.

One very particularly preferred agent contains (a) from about 1.0 to about 13.0% by weight tin(II) oxalate, based on the total weight of the agent.

One very particularly preferred agent contains (a) from about 2.0 to about 11.0% by weight tin(II) oxalate, based on the total weight of the agent.

One very particularly preferred agent contains (a) from about 3.0 to about 10.0% by weight tin(II) oxalate, based on the total weight of the agent.

The agent as contemplated herein contains the metal salt(s) in an aqueous cosmetic carrier. The agent therefore contains water (b) as the second essential ingredient.

The water content (b) in the agent is from about 40.0% by weight to about 99.0% by weight, from about 50.0 to about 97.0% by weight, from about 60.0 to about 95.0% by weight, or from about 70 to about 93.0% by weight. The water content is hereby based on the quantity of the water present in the agent, set in relation to the total weight of the agent.

In another particularly preferred embodiment, an agent as contemplated herein contains, based on the total weight of the agent, (a) from about 40.0% by weight to about 99.0% by weight, from about 50.0 to about 97.0% by weight, from about 60.0 to about 95.0% by weight, or from about 70 to about 93.0% by weight, water.

In the course of the studies leading to the present disclosure, it has also been found that the pH of the agent as contemplated herein may have an important influence on achieving an optimal decolorizing effect. Particularly good results have been obtained when the agent is set to acidic pH values. Agents showed the best effect in the pH range between about 1.0 and about 3.0.

For the agent as contemplated in embodiments herein, the agent has a pH between about 1.0 and about 3.0. The agent very particularly preferably has a pH between about 1.0 and about 2.9, between about 1.0 and about 2.8, between about 1.0 and about 2.7, between about 1.0 and about 2.6, or between about 1.0 and about 2.5.

In another very particularly preferred embodiment, the agent as contemplated herein has a pH between about 1.0 and about 2.9, preferably between about 1.0 and about 2.8, between about 1.0 and about 2.7, between about 1.0 and about 2.6, or between about 1.0 and about 2.5.

The pH values of the present disclosure were measured at a temperature of 22° C., using a model N61 glass electrode from Schott.

The acidic pH may in principle be set using various acids. Examples of suitable acids are citric acid, tartaric acid, malic acid, lactic acid, acetic acid, sulfuric acid, hydrochloric acid, phosphoric acid, methanesulfonic acid, benzoic acid, malonic acid, oxalic acid, and/or 1-hydroxyethane-1,1-diphosphonic acid. The acid(s) from the group comprising citric acid, tartaric acid, malic acid, lactic acid, methanesulfonic acid, oxalic acid, malonic acid, benzoic acid, hydrochloric acid, sulfuric acid, phosphoric acid, and/or 1-hydroxyethane-1,1-diphosphonic acid is/are preferred.

Strong inorganic acids such as sulfuric acid, phosphoric acid, hydrochloric acid, and hydrobromic acid have proven to be very particularly preferably suited for setting the strongly acidic pH ranges.

In another particularly preferred embodiment, an agent as contemplated herein contains one or more inorganic acids chosen from the group of sulfuric acid, phosphoric acid, hydrochloric acid, and hydrobromic acid.

Instead of, or preferably in addition to, the inorganic acids mentioned above, the agent as contemplated herein may contain one or more organic acids chosen from the group of citric acid, tartaric acid, malic acid, lactic acid, acetic acid, hydroxyethane-1,1-diphosphonic acid, methanesulfonic acid, oxaloacetic acid, succinic acid, malonic acid, methanesulfonic acid, and/or oxalic acid.

In another particularly preferred embodiment, an agent as contemplated herein contains one or more organic acids from the group comprising citric acid, tartaric acid, malic acid, lactic acid, acetic acid, hydroxyethane-1,1-diphosphonic acid, methanesulfonic acid, oxaloacetic acid, succinic acid, malonic acid, methanesulfonic acid, and/or oxalic acid.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water, wherein the agent has a pH between about 1.0 and about 3.0.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water, wherein the agent has a pH between about 1.0 and about 2.9.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water, wherein the agent has a pH between about 1.0 and about 2.8.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II)

bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water, wherein the agent has a pH between about 1.0 and about 2.7.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water, wherein the agent has a pH between about 1.0 and about 2.6.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water, wherein the agent has a pH between about 1.0 and about 2.5.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water and (c) one or more inorganic acids from the group comprising sulfuric acid, phosphoric acid, hydrochloric acid, and hydrobromic acid, wherein the agent has a pH between about 1.0 and about 3.0.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water and (c) one or more inorganic acids from the group comprising sulfuric acid, phosphoric acid, hydrochloric acid, and hydrobromic acid, wherein the agent has a pH between about 1.0 and about 2.9.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water and (c) one or more inorganic acids from the group comprising sulfuric acid, phosphoric acid, hydrochloric acid, and hydrobromic acid, wherein the agent has a pH between about 1.0 and about 2.8.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water and (c) one or more inorganic acids from the group comprising sulfuric acid, phosphoric acid, hydrochloric acid, and hydrobromic acid, wherein the agent has a pH between about 1.0 and about 2.7.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water and (c) one or more inorganic acids from the group comprising sulfuric acid, phosphoric acid, hydrochloric acid, and hydrobromic acid, wherein the agent has a pH between about 1.0 and about 2.6.

An agent for treating keratinic fibers, in particular human hair, is particularly preferred which contains in a cosmetic carrier (a) one or more metal salts from the group comprising tin(II) chloride, tin(II) bromide, tin(II) fluoride, tin(II) sulfate, tin(II) oxide, tin(II) hydroxide, tin(II) carbonate, tin(II) phosphate, tin(II) acetate, tin(II) gluconate, tin(II) lactate, tin(II) tartrate, tin(II) oxalate, iron(II) chloride, iron(II) bromide, iron(II) fluoride, iron(II) sulfate, iron(II) oxide, iron(II) hydroxide, iron(II) carbonate, iron(II) phosphate, iron(II) acetate, iron(II) gluconate, iron(II) lactate, iron(II) tartrate, and iron(II) oxalate and (b) water and
(c) one or more inorganic acids from the group comprising sulfuric acid, phosphoric acid, hydrochloric acid, and hydrobromic acid,
wherein the agent has a pH between about 1.0 and about 2.5.

Decolorization of dyed keratin fibers

The agent as contemplated herein is an aftertreatment agent that is used after the decolorization of previously dyed keratinic fibers. The dyed keratin fibers are usually fibers that have been dyed beforehand with conventional oxidation dyes and/or substantive dyes known to those skilled in the art.

The decolorizing agents contain at least one sulfur-containing reducing agent, and are suitable for removing colorations that have been produced on the keratin fibers using oxidation dyes based on developer components and coupler components. The colorations thus produced may be effectively removed, and with virtually no subsequent darkening, by use of the decolorizing agent when the following compounds have been used as developer: p-phenylenediamine, p-toluylenediamine, N,N-bis-(β-hydroxyethyl)-p-phenylenediamine, 4-N,N-bis-(β-hydroxyethyl)amino-2-methylaniline, 2-(β-hydroxyethyl)-p-phenylenediamine, 2-(α,β-dihydroxyethyl)-p-phenylenediamine, 2-hydroxymethyl-p-phenylenediamine, bis-(2-hydroxy-5-aminophenyl) methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine, and/or 4,5-diamino-1-(β-hydroxyethyl)pyrazole.

When the following compounds have been used as coupler, the colorations thus produced may likewise be removed with a very good decolorizing result: m-phenylenediamine derivatives, naphthols, resorcinol and resorcinol derivatives, pyrazolones, and m-aminophenol derivatives. 1-Naphthol, 1,5-, 2,7-, and 1,7-dihydroxynaphthalene, 5-amino-2-methylphenol, m-aminophenol, resorcinol, resorcinol monomethyl ether, m-phenylenediamine, 1-phenyl-3-methyl-pyrazolone-5,2,4-dichloro-3-aminophenol, 1,3-bis-(2',4'-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol, and 2-methyl-4-chloro-5-aminophenol are in particular suited as coupler substances. 1-Naphthol, 1,5-dihydroxynaphthalene, 2,7-dihydroxynaphthalene, 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol, and 2,6-dihydroxy-3,4-dimethylpyridine.

The substrate to be decolorized may likewise have been dyed using substantive dyes. In particular nitrophenylenediamines, nitroaminophenols, azo dyes, anthraquinones, or indophenols are suitable as substantive dyes. Preferred substantive dyes are the compounds known under the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid, and 2-choro-6-ethylamino-1-hydroxy-4-nitrobenzene.

Furthermore, the substrates to be decolorized may also be dyed using naturally occurring, natural dyes such as those contained, for example, in henna red, henna neutral, henna black, chamomile blossom, sandalwood, black tea, black alder bark, sage, logwood, madder root, catechu, cedar, and alkanna root.

The decolorizing agents are intended for removing these colorations, and therefore preferably contain no dyes themselves, i.e., no oxidation dye precursors of the developer type or of the coupler type, and also no substantive dyes.

The aftertreatment agent as contemplated herein used after the decolorization is used to improve and intensify the decolorizing power, and therefore likewise preferably contains no dyes itself.

A common feature of all dyes of the dye classes mentioned above is the presence of an aromatic group in their molecular structure, which is a component of a system of conjugated double bonds, and which thus creates a chromophoric (color-imparting) system. The agents as contemplated herein should have no colorizing properties, and consequently are preferably free of aromatic compounds.

As contemplated herein, the feature "free of aromatic compounds" is understood to mean that the overall quantity of aromatic compounds contained in the agent is less than about 0.1% by weight, preferably less than about 0.05% by weight, and very particularly preferably less than about 0.01% by weight. The overall quantity of aromatic compounds contained in the agent is understood to mean the totality of aromatic and heteroaromatic compounds present in the agent, which is set in relation to the total weight of the agent.

As contemplated herein, a compound is regarded as aromatic when it has at least one aromatic and/or heteroaromatic group in its molecular structure.

An aromatic group is, for example, a (substituted) benzene ring or naphthalene ring. A heteroaromatic compound is, for example, a (substituted) pyridine, pyrimidine, pyrazine, pyrazole, imidazole, thiazole, oxazole, benzimidazole, benzothiazole, benzooxazole, quinoline, quinazoline, or quinoxaline ring.

In another particularly preferred embodiment, an agent as contemplated herein has an overall quantity of aromatic compounds of less than about 0.1% by weight, preferably less than about 0.05% by weight, and very particularly preferably less than about 0.01% by weight, based on the total weight of the agent.

As already described above, the agent as contemplated herein is used after the reductive decolorization of dyed keratinic fibers, and itself contains no metal salts having a reducing effect. For reasons of incompatibility and to avoid uncontrollable exothermic reactions, the agent therefore preferably contains no oxidizing agents, in particular no oxidizing agents from the group of peroxo compounds.

As contemplated herein, an oxidizing agent is regarded as a peroxo compound when it has at least one peroxo group —O—O— in its molecular structure.

Oxidizing agents from the group of peroxo compounds are hereby understood to mean, for example, hydrogen peroxide, persulfates (potassium persulfate (alternatively, potassium peroxodisulfate), sodium persulfate (sodium peroxodisulfate), and ammonium persulfate (alternatively, ammonium peroxodisulfate)), and percarbonates (sodium percarbonate, potassium percarbonate, for example). The agent as contemplated herein preferably contains none of the oxidizing agents mentioned above.

In another particularly preferred embodiment, an agent as contemplated herein has an overall quantity of oxidizing agents from the group of peroxo compounds of less than about 0.1% by weight, less than about 0.05% by weight, or less than about 0.01% by weight, based on the total weight of the agent.

The agent is provided as an aqueous preparation to which further surface-active ingredients may also be added. These are preferably selected from the group of nonionic, anionic, zwitterionic, amphoteric, and/or cationic surfactants.

In another particularly preferred embodiment, an agent as contemplated herein contains one or more surfactants from the group of nonionic, anionic, zwitterionic, amphoteric, and/or cationic surfactants.

It has proven to be advantageous when the agent contains nonionogenic surface-active ingredients. Preferred nonionic surfactants are alkyl polyglycosides and alkylene oxide addition products with fatty alcohols, fatty acids, and fatty acid glycerides, in each case having 2 to 50 moles of ethylene oxide per mole of fatty alcohol or fatty acid. Preparations having excellent properties are likewise obtained when they contain fatty acid esters of ethoxylated glycerin as nonionic surfactants. It is very particularly preferred when the agent (b) contains as nonionic surfactant an ethoxylated castor oil in each case having 2 to 50 moles of ethylene oxide per mole of fatty acid, or an ethoxylated, hydrogenated castor oil in each case having 2 to 50 moles of ethylene oxide per mole of fatty acid. In this regard, use of PEG-40 Castor Oil is particularly preferred.

As anionic surfactants, the agent may contain, for example, fatty acids, alkyl sulfates, alkyl ether sufates, and ethercarboxylic acids having 10 to 20 C atoms in the alkyl group and up to 16 glycol ether groups in the molecule.

The agent as contemplated herein may also contain one or more zwitterionic surfactants such as betaines, N-alkyl-N, N-dimethylammonium glycinates, N-acylaminopropyl-N, N-dimethylammonium glycinates, and 2-alkyl-3-carboxymethyl-3-hydroxyethyl imidazolines.

Agents suited as contemplated herein additionally contain at least one amphoteric surfactant. Preferred amphoteric surfactants are N-alkyl glycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids. Particularly preferred amphoteric surfactants are N-cocoalkylamino propionate, cocoacylaminoethylamino propionate, and C12-C18 acyl sarcosine.

Likewise preferred as contemplated herein are cationic surfactants of the quaternary ammonium compound, esterquat, and amidoamine types. Preferred quaternary ammonium compounds are ammonium halides, in particular chlorides and bromides such as alkyltrimethylammonium chlorides, dialkyldimethylammonium chlorides, and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, and the imidazolium compounds known under the INCI names Quaternium-27 and Quaternium-83. The long alkyl chains of the above-mentioned surfactants preferably have 10 to 18 carbon atoms. Quaternized protein hydrolysates are further cationic surfactants that are usable as contemplated herein.

The alkylamidoamines are typically prepared by amidation of natural or synthetic fatty acids and fatty acid cuts with dialkylaminoamines, and in addition to a good conditioning effect are characterized in particular by their good biodegradability. One compound from this substance group that is particularly suitable as contemplated herein is stearamidopropyldimethylamine, commercially available under the name Tegoamid® S 18.

Quaternary ester compounds, so-called esterquats, likewise have very good biodegradability. Esterquats are known substances that contain at least one ester function and at least one quaternary ammonium group as structural elements. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are marketed under the trademarks Stepantex®, Dehyquart®, and Armocare®, for example. The products Armocare® VGH-70, (N,N-bis(2-palmitoyloxyethyl)dimethylammonium chloride), and Dehyquart® F-75, Dehyquart® C-4046, Dehyquart® L80, and Dehyquart® AU-35 are examples of such esterquats.

The cationic surfactants are preferably contained in the agents used as contemplated herein in quantities of from about 0.05 to about 10% by weight, based on the overall agent. Quantities of from about 0.1 to about 5% by weight are particularly preferred.

The nonionic, anionic, zwitterionic, amphoteric, and/or cationic surfactants are used in proportions of from about 0.1 to about 15.0% by weight, from about 0.5 to about 10.0% by weight, or from about 0.7 to about 5.0% by weight, based on the overall quantity of the agent.

In addition, the agents as contemplated herein may contain further active ingredients, auxiliary agents, and additives, for example nonionic polymers such as vinylpyrrolidinone/vinyl acrylate copolymers, polyvinylpyrrolidinone, vinylpyrrolidinone/vinyl acetate copolymers, polyethylene glycols, and polysiloxanes; additional silicones such as volatile or nonvolatile, straight-chain, branched, or cyclic, crosslinked or uncrosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy, and/or hydroxyl groups (dimethicone copolyols), linear polysiloxane (A)-polyoxyalkylene-(B) block copolymers, grafted silicone polymers; cationic polymers such as quaternized cellulose ethers, polysiloxanes having quaternary groups, dimethyldiallylammonium chloride polymers, acrylamide-diethyldiallylammonium chloride copolymers, dimethylaminoethyl methacrylate-vinylpyrrolidinone copolymers or vinylpyrrolidinone-imidazolinium-methochloride copolymers quaternized with diethyl sulfate, and quaternized polyvinyl alcohol; zwitterionic and amphoteric polymers; anionic polymers such as polyacrylic acids or crosslinked polyacrylic acids; structurizers such as glucose, maleic acid, and lactic acid, hair-conditioning compounds such as phospholipids, for example lecithin and cephalins; fragrance oils, dimethyl isosorbide, and cyclodextrins; fiber structure-improving active ingredients, in particular mono-, di-, and oligosaccharides such as glucose, galactose, fructose, fruit sugar, and lactose; dyes for coloring the agent; anti-dandruff active ingredients such as piroctone olamine, zinc omadine, and climbazole; amino acids and oligopeptides; animal- and/or plant-based protein hydrolysates, and in the form of their fatty acid condensation products or optionally anionically or cationically modified derivatives; plant oils; light protection agents and UV blockers; active ingredients such as panthenol, pantothenic acid, pantolactone, allantoin, pyrrolidinone carboxylic acids and the salts thereof, and bisabolol; polyphenols, in particular hydroxycinnamic acids, 6,7-dihydroxycoumarin, hydroxybenzoic acids, catechins, tannins, leucoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling agents and penetration agents such as glycerin, propylene glycol monoethyl ether, carbonates, hydrogen carbonates, guanidines, ureas, and primary, secondary, and tertiary phosphates; opacifiers such as latex, styrene/PVP and styrene/acrylamide copolymers; pearlescing agents such as ethylene glycol mono- and distearate and PEG-3-distearate; pigments, and propellants such as propane-butane mixtures, $N_2O$, dimethyl ether, $CO_2$, and air. In this regard, explicit reference is made to the known monographs, for example Kh. Schrader, Grundlagen and Rezepturen der Kosmetika, 2nd Edition, Htithig Buch Verlag, Heidelberg, 1989, which reflect the relevant knowledge of those skilled in the art.

Method

The agents described above are used as contemplated herein as aftertreatment agents in the method for the reductive decolorization of dyed keratinic fibers.

A second subject matter of the present disclosure is a method for the reductive decolorization of dyed keratinic fibers, comprising the following steps in the stated sequence:
(I) applying a decolorizing agent, containing at least one sulfur-containing reducing agent, to keratinic fibers,
(II) allowing the decolorizing agent to act, preferably for a period of from about 5 to about 120 minutes, from about 10 to about 100 minutes, from about 20 to about 80 minutes, or from about 30 to about 65 minutes,
(III) optionally rinsing the decolorizing agent from the keratinic fibers,
(IV) applying an aftertreatment agent to the keratinic fibers, wherein the aftertreatment agent is an agent as disclosed in detail in the description of the first subject matter as contemplated herein,
(V) allowing the aftertreatment agent to act for a period of from about 30 seconds to about 45 minutes, from about 30 seconds to about 30 minutes, from about 30 seconds to about 20 minutes, or from about 30 seconds to about 10 minutes, and
(VI) optionally rinsing the aftertreatment agent from the keratinic fibers.

In other words, a second subject matter of the present disclosure is a method for the reductive decolorization of dyed keratinic fibers, comprising the following steps in the stated sequence:
(I) applying a decolorizing agent, containing at least one sulfur-containing reducing agent, to keratinic fibers,
(II) allowing the decolorizing agent to act, preferably for a period of from about 5 to about 120 minutes, from about 10 to about 100 minutes, from about 20 to about 80 minutes, or from about 30 to about 65 minutes,
(III) optionally rinsing the decolorizing agent from the keratinic fibers,
(IV) applying an aftertreatment agent to the keratinic fibers,
(V) allowing the aftertreatment agent to act for a period of from about 30 seconds to about 45 minutes, from about 30 seconds to about 30 minutes, from about 30 seconds to about 20 minutes, or from about 30 seconds to about 10 minutes, and
(VI) optionally rinsing the aftertreatment agent from the keratinic fibers,
wherein the aftertreatment agent contains in a cosmetic carrier
(a) one or more metal salts from the group of tin(II) salts, iron(II) salts, manganese(II) salts, titanium(II) salts, and titanium(III) salts and
(b) water
and has a pH between about 1.0 and about 3.0.

Steps (I) and (II) of the method represent the decolorization process for the keratin fibers, and therefore are carried out one after the other in direct succession. If the decolorizing agent is rinsed off in step (III), step (III) directly follows step (II).

In principle, there is no time limitation for the sequence of steps (IV), (V), and (VI). Thus, step (IV) may take place hours, days, or, for example, even up to two weeks after completion of step (III).

It is likewise possible and contemplated herein to carry out the decolorization steps (I) through (VI) multiple times in succession.

The aftertreatment agent as contemplated herein is used in particular to improve the overall decolorizing power and prevent redarkening or reoxidation caused by the action of atmospheric oxygen on the decolorized keratin fibers. In order to effectively prevent this reoxidation, the aftertreatment should take place before the atmospheric oxygen has time to act on the reduced keratin fibers. For this reason, if possible the aftertreatment should take place directly following the decolorization (i.e., directly after completion of method step (III)). It is therefore preferred when there is a period of about 12 hours maximum, about 6 hours maximum, about 1 hour maximum, or about 30 minutes maximum, between the completion of method step (III) and the beginning of method step (IV).

In one preferred method as contemplated herein there is a period of about 12 hours maximum, about 6 hours maximum, about 1 hour maximum, or about 30 minutes maximum, between method steps (III) and (IV).

The decolorizing agent applied in step (I) of the method as contemplated herein contains at least one sulfur-containing reducing agent. In this regard, the sulfur-containing reducing agent(s) already described above as possible decolorizing agents is/are used.

In one particularly preferred embodiment, a method as contemplated herein employs the decolorizing agent that contains one or more sulfur-containing reducing agents from the group comprising formamidine sulfinic acid (($H_2N$)(NH)$C(SO_2H)$), sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethanesulfinic acid, aminomethanesulfinic acid, cysteine, thiolactic acid, thioglycolic acid, disodium [(sulfinatomethyl)amino]methanesulfinate (HN($CH_2SO_2Na$)$_2$), dipotassium [(sulfinatomethyl)amino]methanesulfinate (HN($CH_2SO_2K$)$_2$), [(sulfinomethyl)amino]methanesulfinic acid (HN($CH_2SO_2H$)$_2$), trisodium [bis(sulfinatomethyl)amino]methanesulfinate (N($CH_2SO_2Na$)$_3$), tripotassium [bis(sulfinatomethyl)amino]methanesulfinate (N($CH_2SO_2K$)$_3$), [bis(sulfinomethyl)amino]methanesulfinic acid (N($CH_2SO_2H$)$_3$), sodium 1-aminoethane-1-sulfinate ($H_2NCH(CH_3)SO_2Na$), potassium 1-aminoethane-1-sulfinate ($H_2NCH(CH_3)SO_2K$), 1-aminoethane-1-sulfinic acid ($H_2NCH(CH_3)SO_2H$), disodium 1-[(1-sulfinatoethyl)amino]ethane-1-sulfinate ($HN(CH(CH_3)SO_2Na)_2$), dipotassium 1-[(1-sulfinatoethyl)amino]ethane-1-sulfinate ($HN(CH(CH_3)SO_2K)_2$), 1-[(1-sulfinoethyl)amino]ethane-1-sulfinic acid ($HN(CH(CH_3)SO_2H)_2$), trisodium 1-[bis(1-sulfinatoethyl)amino]ethane-1-sulfinate ($N(CH(CH_3)SO_2Na)_3$), tripotassium 1-[bis(1-sulfinatoethyl)amino]ethane-1-sulfinate ($N(CH(CH_3)SO_2K)_3$), and 1-[bis(1-sulfinoethyl)amino]ethane-1-sulfinic acid ($N(CH(CH_3)SO_2H)_3$).

A method for the reductive decolorization of dyed keratinic fibers is particularly preferred which comprises the following steps in the stated sequence:
(I) applying a decolorizing agent, containing at least one sulfur-containing reducing agent, to keratinic fibers,
(II) allowing the decolorizing agent to act, preferably for a period of from about 5 to about 120 minutes, from about 10 to about 100 minutes, from about 20 to about 80 minutes, or from about 30 to about 65 minutes,
(III) rinsing the decolorizing agent from the keratinic fibers,
(IV) applying an aftertreatment agent to the keratinic fibers, wherein the aftertreatment agent is an agent as disclosed in detail in the description of the first subject matter as contemplated herein,
(V) allowing the aftertreatment agent to act for a period of from about 30 seconds to about 30 minutes, from about 30 seconds to about 20 minutes, from about 30 seconds to about 10 minutes, or from about 30 seconds to about 5 minutes, and
(VI) rinsing the aftertreatment agent from the keratinic fibers.

A method for the reductive decolorization of dyed keratinic fibers is thus particularly preferred in which
(III) the decolorizing agent is rinsed from the keratinic fibers and
(VI) the aftertreatment agent is rinsed from the keratinic fibers.

The application of the aftertreatment agent may also be repeated multiple times, for example when the aftertreatment agent is present in the form of a shampoo that is regularly used after the decolorization. Within the scope of this embodiment, the aftertreatment agent preferably additionally contains one or more surfactants. If the aftertreatment, i.e., carrying out steps (IV) through (VI), is repeated regularly, it is possible to suppress the reoxidation for a particularly long period of time.

In another preferred embodiment, the aftertreatment agent may also be provided as a "leave-on" product that remains on the keratinic fibers after being applied. When the agent is designed as a "leave-on" product, it preferably contains no, or only small quantities of, surfactants.

Therefore, a method for the reductive decolorization of dyed keratinic fibers is also particularly preferred which comprises the following steps in the stated sequence:
(I) applying a decolorizing agent, containing at least one sulfur-containing reducing agent, to keratinic fibers,
(II) allowing the decolorizing agent to act, preferably for a period of from about 5 to about 120 minutes, from about 10 to about 100 minutes, from about 20 to about 80 minutes, or from about 30 to about 65 minutes,
(III) rinsing the decolorizing agent from the keratinic fibers,
(IV) applying an aftertreatment agent to the keratinic fibers, wherein the aftertreatment agent is an agent as disclosed in detail in the description of the first subject matter as contemplated herein,
(V) allowing the aftertreatment agent to act,
(VI) not rinsing the aftertreatment agent from the keratinic fibers.

Since the aftertreatment agent is not rinsed out in this embodiment, in principle the method as contemplated herein ends with step (V).

Therefore, a method for the reductive decolorization of dyed keratinic fibers is also particularly preferred which comprises the following steps in the stated sequence:
(I) applying a decolorizing agent, containing at least one sulfur-containing reducing agent, to keratinic fibers,
(I) allowing the decolorizing agent to act, for example for a period of from about 5 to about 120 minutes, from about 10 to about 100 minutes, from about 20 to about 80 minutes, or from about 30 to about 65 minutes,
(II) rinsing the decolorizing agent from the keratinic fibers,
(III) applying an aftertreatment agent to the keratinic fibers, wherein the aftertreatment agent is an agent as disclosed in detail in the description of the first subject matter as contemplated herein,
(IV) allowing the aftertreatment agent to act.

The statements concerning the multicomponent packaging unit as contemplated herein apply mutatis mutandis with regard to further preferred embodiments of the method as contemplated herein.

EXAMPLES 1.1. Coloration
The following formulations were prepared (all entries are in % by weight):
Color cream (F1)

|  | % by weight |
|---|---|
| Cetearyl alcohol | 3.4 |
| C12-C18 fatty alcohols | 1.2 |
| Ceteareth-20 | 0.3 |
| Ceteareth-12 | 0.3 |
| Lamesoft PO 65 (Coco-Glucoside, Glyceryl Oleate, Water) | 1.00 |
| Sodium Laureth-6 Carboxylate (21% aqueous solution) | 4.91 |
| Sodium Myreth Sulfate (68-73% aqueous solution) | 1.38 |
| Paraffinum Liquidum | 0.29 |
| Sodium acrylate, trimethylammoniopropylacrylamide chloride copolymer (19-21% aqueous solution) | 1.84 |
| p-Toluylenediamine, sulfate | 0.88 |
| Resorcinol | 0.30 |
| 2-Methylresorcinol | 0.04 |
| 2-Amino-3-hydroxypyridine | 0.05 |
| m-Aminophenol | 0.05 |
| Sodium sulfite | 0.2 |
| Ascorbic acid | 0.05 |
| 1-Hydroxyethane-1,1-diphosphonic acid (60% aqueous solution) | 0.1 |
| Sodium hydroxide (50% aqueous solution) | 0.54 |
| Sodium silicate 40/42 | 0.25 |
| Ammonia (25% aqueous solution) | 3.19 |
| Water | To make 100 |

Oxidizing agent (Ox)

|  | % by weight |
|---|---|
| Sodium hydroxide | 0.39 |
| Dipicolinic acid | 0.05 |
| Disodium pyrophosphate | 0.02 |
| Sodium laureth sulfate (3 EO) | 1.02 |
| 1-Hydroxyethane-1,1-diphosphonic acid (60% aqueous solution) | 0.76 |
| Aculyn 33 A (Acrylates Copolymer) | 7.63 |
| Hydrogen peroxide (50% aqueous solution) | 6.1 |
| Water | To make 100 |

The color cream (F1) and the oxidizing agent (Ox) were mixed in a 1:1 quantity ratio and applied to hair strands (Kerling Euronaturhaar, white). The weight ratio of application mixture to hair was 4:1, and the exposure time was 30 minutes at a temperature of 32 degrees Celsius. The strands were subsequently rinsed with water, dried, and allowed to rest for at least 24 hours at room temperature. The strands were dyed in a medium brown shade. The hairs were measured colorimetrically.

1.2. Decolorization

The following decolorizing agents were prepared (all entries in % by weight of active ingredient):

Agent (I)

| Agent (I) | % by weight |
| --- | --- |
| Versagel M 1600[(1)] | 4.25 |
| Lanette N[(2)] | 6.00 |
| Ceteareth-20 (C16-C18 fatty alcohol, ethoxylated with 20 EO) | 0.50 |
| Ceteareth-50 (C16-C18 fatty alcohol, ethoxylated with 50 EO) | 2.75 |
| Formamidine sulfinic acid | 50 |
| Paraffinium Liquidum | To make 100 |

[(1)]INCI: Paraffinium Liquidum (Mineral Oil), Ethylene/Propylene/Styrene Copolymer, Butylene/Ethylene/Styrene Copolymer
[(2)]INCI: Cetearyl Alcohol (approximately 90%) and Sodium Cetearyl Sulfate (approximately 10.0%)

Agent (II)

| Agent (II) | % by weight |
| --- | --- |
| Monoethanolamine | 2.0 |
| Emulgade F[(3)] | 3.0 |
| Water (distilled) | To make 100 |

[(3)]Cetearyl Alcohol, PEG-40 Castor Oil, Sodium Cetearyl Sulfate

The agents (I) and (II) were mixed together in an (a)/(c) quantity ratio of 1:4 (i.e., 20 g agent (a) and 80 g agent (c)).

The ready-to-use decolorizing agents (OHIO) prepared in this way were each applied to the hairs colored according to item 1.1 and allowed to act for 30 minutes. The strands were subsequently rinsed with water for 20 seconds.

One of the following aftertreatment agents was then applied in each case to the still moist strands. The aftertreatment agent was allowed to act for 30 minutes. The strands were subsequently rinsed with water and dried in air for 2 days.

Aftertreatment agent (all entries in % by weight)

| | V | E1 | E2 | E3 | E4 | E5 |
| --- | --- | --- | --- | --- | --- | --- |
| Tin(II) fluoride ($SnF_2$) | — | 5.0 | 5.0 | — | — | — |
| Tin(II) chloride ($SnCl_2$) | — | — | — | 5.0 | — | — |
| Iron(II) chloride ($FeCl_2$) | — | — | — | — | 5.0 | 5.0 |
| Sulfuric acid | pH 2.3 | pH 2.3 | pH 1.5 | pH 1.5 | pH 2.8 | pH 1.5 |
| Emulgade F[(3)] | 3.0 | 3.0 | 3.0 | 3.0 | 3.0 | 3.0 |
| Water | To make 100 | To make 100 | To make 100 | To make 100 | To make 100 | To make 100 |

[(3)]Cetearyl Alcohol, PEG-40 Castor Oil, Sodium Cetearyl Sulfate

The hairs were once again measured colorimetrically.

For determining the decolorizing effect, the $\Delta L$ value was determined according to the following formula:

$$\Delta L = L(\text{after the decolorization}) - L(\text{after the coloration})$$

Within the Lab color space, the L axis describes the lightness of a color (L=0 means black, L=100 means white). The larger the $\Delta L$ value, the greater the difference in the lightness of the color, and the more intensely the hair is decolorized. A decolorizing agent has a better effect the higher the $\Delta L$ value.

| Aftertreatment agent | L | a | b | $\Delta L$ |
| --- | --- | --- | --- | --- |
| V (pH 2.3) | 21.69 | 7.38 | 7.71 | 4.6 |
| E1 ($SnF_2$, pH 2.3) | 42.61 | 9.51 | 22.49 | 25.5 |
| E2 ($SnF_2$, pH 1.5) | 42.18 | 10.41 | 22.23 | 25.1 |
| E3 ($SnCl_2$, pH 1.5) | 42.60 | 9.35 | 21.44 | 25.5 |
| E4 ($FeCl_2$, pH 2.8) | 22.64 | 5.51 | 8.09 | 5.5 |
| E5 ($FeCl_2$, pH 1.5) | 25.93 | 8.01 | 11.26 | 8.8 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for treating keratinic fibers, comprising:
    (a) one or more metal salts chosen from tin(II) fluoride or tin(II) chloride, wherein, based on the total weight of the agent, the (a) one or more metal salts are present in an overall quantity of from 3.0 to about 10.0% by weight,
    (b) water, wherein, based on the total weight of the agent, the (b) water is present in an overall quantity of from about 70 to 93.0% by weight,
    (c) one or more acids chosen from inorganic acids or organic acids, and
    (d) one or more surfactants chosen from nonionic, anionic, zwitterionic, amphoteric, or cationic surfactants,
    wherein an overall quantity of aromatic compounds present in the agent is less than about 0.1% by weight, based on the total weight of the agent,
    wherein an overall quantity of oxidizing agents chosen from peroxo compounds is present in the agent in an amount less than about 0.1% by weight, based on the total weight of the agent, and
    wherein the agent has a pH between about 1.0 and about 2.5.

2. The agent according to claim 1, comprising one or more inorganic acids chosen from sulfuric acid, phosphoric acid, hydrochloric acid, or hydrobromic acid.

3. The agent according to claim 1, comprising one or more organic acids chosen from citric acid, tartaric acid, malic acid, lactic acid, acetic acid, hydroxyethane-1,1-diphosphonic acid, methanesulfonic acid, oxaloacetic acid, succinic acid, malonic acid, methanesulfonic acid, or oxalic acid.

4. The agent according to claim 1, wherein an overall quantity of aromatic compounds present in the agent is less than about 0.01% by weight, based on the total weight of the agent.

5. The agent according to claim 1, wherein an overall quantity of oxidizing agents chosen from peroxo compounds is present in the agent in an amount less than about 0.01% by weight, based on the total weight of the agent.

6. A method for the reductive decolorization of dyed keratinic fibers, comprising the following steps in the stated sequence:
(I) applying a decolorizing agent, comprising at least one sulfur-containing reducing agent, to keratinic fibers,
(II) allowing the decolorizing agent to act,
(III) optionally rinsing the decolorizing agent from the keratinic fibers,
(IV) applying an aftertreatment agent to the keratinic fibers, wherein the aftertreatment agent is an agent comprising (a) one or more metal salts chosen from tin(II) fluoride or tin(II) chloride, wherein, based on the total weight of the agent, the (a) one or more metal salts are present in an overall quantity of from 3.0 to about 10.0% by weight, (b) water, wherein, based on the total weight of the agent, the (b) water is present in an overall quantity of from about 70 to 93.0% by weight, (c) one or more acids chosen from inorganic acids or organic acids, and (d) one or more surfactants chosen from nonionic, anionic, zwitterionic, amphoteric, or cationic surfactants, wherein an overall quantity of aromatic compounds present in the agent is less than about 0.1% by weight, based on the total weight of the agent, wherein an overall quantity of oxidizing agents chosen from peroxo compounds is present in the agent in an amount less than about 0.1% by weight, based on the total weight of the agent, and wherein the aftertreatment agent has a pH between 1.0 and 2.5,
(V) allowing the aftertreatment agent to act for a period of time, optionally from about 30 seconds to about 45 minutes, and
(VI) optionally rinsing the aftertreatment agent from the keratinic fibers.

7. The method according to claim 6, wherein the decolorizing agent comprises one or more sulfur-containing reducing agents chosen from the group of formamidine sulfinic acid, sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethanesulfinic acid, aminomethanesulfinic acid, cysteine, thiolactic acid, thioglycolic acid, disodium [(sulfinatomethyl)amino]methanesulfinate, dipotassium [(sulfinatomethyl)amino]methanesulfinate, [(sulfinomethyl)amino]methanesulfinic acid, trisodium [bis(sulfinatomethyl)amino]methanesulfinate, tripotassium [bis(sulfinatomethyl)amino]methanesulfinate, [bis(sulfinomethyl)amino]methanesulfinic acid, sodium 1-aminoethane-1-sulfinate, potassium 1-aminoethane-1-sulfinate, 1 aminoethane-1-sulfinic acid, disodium 1-[(1-sulfinatoethyl)amino]ethane-1-sulfinate, dipotassium 1-[(1-sulfinatoethyl)amino]ethane-1-sulfinate, 1-[(1-sulfinoethyl)amino]ethane-1-sulfinic acid, trisodium 1-[bis(1-sulfinatoethyl)amino]ethane-1-sulfinate, tripotassium 1-[bis(1-sulfinatoethyl)amino]ethane-1-sulfinate, or 1-[bis(1-sulfinoethyl)amino]ethane-1-sulfinic acid.

8. The method according to claim 6, wherein
(III) the decolorizing agent is rinsed from the keratinic fibers and
(VI) the aftertreatment agent is rinsed from the keratinic fibers.

* * * * *